US011531125B2

(12) United States Patent
Xu et al.

(10) Patent No.: US 11,531,125 B2
(45) Date of Patent: Dec. 20, 2022

(54) THREE-DIMENSIONALLY HETEROGENEOUS PET SYSTEM

(71) Applicant: RAYCAN TECHNOLOGY CO., LTD. (SU ZHOU), Suzhou (CN)

(72) Inventors: Hao Xu, Suzhou (CN); Shuai Wang, Suzhou (CN); Qingguo Xie, Suzhou (CN); Huihua Wen, Suzhou (CN)

(73) Assignee: RAYCAN TECHNOLOGY CO., LTD (SUZHOU), Suzhou (CN)

( * ) Notice: Subject to any disclaimer, the term of this patent is extended or adjusted under 35 U.S.C. 154(b) by 189 days.

(21) Appl. No.: 16/480,661

(22) PCT Filed: Oct. 27, 2017

(86) PCT No.: PCT/CN2017/108073
§ 371 (c)(1),
(2) Date: Jul. 24, 2019

(87) PCT Pub. No.: WO2018/214400
PCT Pub. Date: Nov. 29, 2018

(65) Prior Publication Data
US 2021/0132241 A1    May 6, 2021

(30) Foreign Application Priority Data
May 25, 2017 (CN) .......................... 201710378448.0

(51) Int. Cl.
*G01T 1/29* (2006.01)
*A61B 6/03* (2006.01)
(Continued)

(52) U.S. Cl.
CPC ............ *G01T 1/2985* (2013.01); *A61B 6/037* (2013.01); *A61B 6/4208* (2013.01); *G06T 7/0012* (2013.01); *G06T 15/00* (2013.01)

(58) Field of Classification Search
CPC ..... G01T 1/161; G01T 1/1644; G01T 1/2008; G01T 1/20182; G01T 1/2018;
(Continued)

(56) References Cited

U.S. PATENT DOCUMENTS

| 2016/0209515 A1* | 7/2016 | Da Silva Rodrigues ................... G01T 1/1603 |
| 2018/0011205 A1* | 1/2018 | Lin ...................... G01T 1/2008 |

(Continued)

FOREIGN PATENT DOCUMENTS

CN    104614754 A  *  5/2015  ........... G01T 1/1642

OTHER PUBLICATIONS

Moses, William W. "Fundamental limits of spatial resolution in PET." Nuclear Instruments and Methods in Physics Research Section A: Accelerators, Spectrometers, Detectors and Associated Equipment 648 (2011): S236-S240.*

(Continued)

*Primary Examiner* — Carolyn A Pehlke
(74) *Attorney, Agent, or Firm* — William H. Honaker; Dickinson Wright PLLC

(57) ABSTRACT

The application provides a three-dimensionally heterogeneous PET system comprising at least two heterogeneous detector modules, each comprising at least two kinds of crystal strips closely arranged to form different detection performances levels for different kinds of crystal strips and same detection performances levels for same kind of crystal strips. Parameters of detection performances of crystal strips comprise energy resolution, density, size and light output, wherein different detection performances levels for crystal strips comprise one or more of parameters of detection performances of crystal strips being in different levels. Compared with a high spatial resolution PET system, the application effectively reduces manufacturing costs of a PET (Continued)

system without significantly reducing spatial resolution thereof. Compared with an ordinary spatial resolution PET system, it improves spatial resolution of a PET system by slightly increasing its cost, and can also provide imaging field of view with high spatial resolution in radial direction.

10 Claims, 3 Drawing Sheets

(51) Int. Cl.
*A61B 6/00* (2006.01)
*G06T 7/00* (2017.01)
*G06T 15/00* (2011.01)

(58) Field of Classification Search
CPC ..... G01T 1/202; G01T 1/2023; G01T 1/2985; A61B 6/037; A61B 6/4258; A61B 6/4266; A61B 6/4208
See application file for complete search history.

(56) References Cited

U.S. PATENT DOCUMENTS

2018/0184992 A1* 7/2018 Li ................. A61B 6/037
2019/0261934 A1* 8/2019 Seo ............... A61B 6/4429

OTHER PUBLICATIONS

Cherry, Simon R., and Magnus Dahlbom. "PET: physics, instrumentation, and scanners." In PET, pp. 1-117. Springer, New York, NY, 2006.*
Cox, Benjamin L., et al. "Development of a novel linearly-filled Derenzo microPET phantom." American journal of nuclear medicine and molecular imaging 6.3 (2016): 199.*
Ghazanfari, Nafise, et al. "Quantitative assessment of crystal material and size on the performance of rotating dual head small animal PET scanners using Monte Carlo modeling." Hellenic journal of nuclear medicine 15.1 (2012): 33-39.*
Yin, Yongzhi, et al. "Evaluation of PET Imaging Resolution Using 350u Pixelated CZT as a VP-PET Insert Detector." IEEE Transactions on Nuclear Science 61.1 (2014): 154-161.*
Mathews, Aswin John, et al. "Improving PET imaging for breast cancer using virtual pinhole PET half-ring insert." Physics in Medicine & Biology 58.18 (2013): 6407.*

* cited by examiner ental Patent Application Serial No. PCT/CN2017/108073,
THREE-DIMENSIONALLY HETEROGENEOUS PET SYSTEM

CROSS-REFERENCE TO RELATED APPLICATION

The present invention claims the benefit of PCT International Patent Application Serial No. PCT/CN2017/108073, filed on Oct. 27, 2017 which claims priority to Chinese Patent Application Serial No. CN201710378448.0 filed on May 25, 2017, the entire disclosure of which are considered as part of the disclosure of this application and are hereby incorporated by reference.

FIELD OF THE INVENTION

The present application relates to a positron emission tomography system in the field of nuclear medicine, in particular to a three-dimensionally heterogeneous PET system.

BACKGROUND OF THE INVENTION

PET (Positron Emission Tomography, referred to as PET) is a large, sophisticated nuclear medical imaging equipment, the imaging principle of which is to inject the tracer with biological activity and with radioactivity into a living body, the tracer participating in the metabolism of the living body and presenting different distribution in the living body along with the different metabolic levels, and then to image the distribution of the tracer in the living body. PET can evaluate the metabolic levels, biochemical reactions and functional activities of various organs in the living body noninvasively, quantitatively, dynamically at the cellular level, and thus can detect the related biochemical changes before the structural changes or symptomatic deterioration caused by many diseases. PET has great and unique application value for the diagnosis and treatment to serious diseases, especially to tumor, cardiovascular disease and nervous system disease.

One important performance index of the PET system is spatial resolution, which represents that the minimal size between two target points in the images can be distinguished by the PET system. The better the spatial resolution, the clearer the image. Thus it can provide more references for clinical diagnosis and treatment.

In the present field of PET study, there are the systems including the annular PET system, the Flat PET system, the two-dimensional annular heterogeneous detector PET system and the adaptive PET system according to the arrangement forms of the PET detectors.

The annular PET system is the most commonly and widely used in the market, and the detector module of which is constructed by crystal strips with the same performances. Since the limitation of the spatial resolution is about ½ of the size of the crystal strips in the homogeneous PET system, the purpose of improving the spatial resolution of PET system can be only realized by improving the performance of the crystal strip. However, the costs are dramatically increased as the performances of the crystal strips become higher. For example, on the premise of keeping the imaging field of view of the same size, it will leads to a problem about extremely high cost for detector module to be composed wholly of high performance crystal strips in order to meet the requirements in aspect of spatial resolution of system.

The flat PET system is set up of two symmetrical PET detector modules, which is quite different from the annular PET system in aspect of the contour. The advantage of the system is reducing the manufacturing cost of the PET system. However, the undersampling and the corresponding incomplete information available causes the PET system showing imaging artifacts, which instead reduces the spatial resolution of some positions.

The two-dimensional annular heterogeneous detector (heterogeneous means that the detector module of the system is composed of crystal strips with different performances) PET system is also annular structure, wherein parts of the detector modules use high performance crystal strips and other parts of the detector modules use ordinary crystal strips (e.g. Jingjing Liu, etc. A PET system design by using mixed detectors: resolution properties). On the one hand, the two-dimensional annular heterogeneous detector PET system reduces the use of high performance crystal strips to a certain extent and thus decreases the costs; on the other hand, it is limited to two dimensional imaging.

The adaptive PET system (e.g. CN101856236A) selects different detector modules each of which adopts crystal strips with the same performances, namely, with exactly the same parameters such as dimension, size, material, energy resolution, etc. Unfortunately, the system cannot meet the requirements of the spatial resolution under certain situations.

On the one hand, the requirements of the PET system in spatial resolution are very strict when imaging certain parts of a living body; on the other hand, the requirements are not strict as to some other parts of the same living body. Thus, if the PET system uses ordinary performance crystal strips entirely, it will lead to the failure of meeting the requirements of the PET system in spatial resolution, on the contrary, if the PET system uses high performance crystal strips entirely, it will lead to the increase of the system cost and failure of fully utilizing the overall performance of the system. For example, when imaging the brains and hearts of mice, the PET system requires a high spatial resolution, but when imaging the bladders of mice, the PET system does not require such a high spatial resolution as the brains and hearts. Whether it's an annular PET system or a flat PET system, these problems can occur. The appearance of the two-dimensional annular heterogeneous detector PET system and the adaptive PET system solve the problem to some extent. However, both systems use intra-annular heterogeneous, namely, the detector modules are the same and the crystal stripes used between them have the same performance in axial direction. In this kind of system, if the imaged bodies require high spatial resolution imaging field of view or high spatial resolution imaging field of view in radial direction, the detector systems in the above two kinds of structures can't satisfy their requirements.

SUMMARY OF THE INVENTION

The purpose according to the present application is to provide a three-dimensionally heterogeneous PET system so as to be able to balance the cost and high spatial resolution imaging in special location.

Thus the technical solution of the present application is to provide a three-dimensionally heterogeneous PET system which includes at least two heterogeneous detector modules, each of which includes at least two kinds of crystal strips that are closely arranged to form different detection performances levels for different kinds of crystal strips and same detection performances levels for same kind of crystal strips. The parameters of detection performances of crystal strips comprise energy resolution, density, size and light output, etc.; wherein different detection performances levels for crystal strips comprise one or more of the parameters of detection performances of crystal strips being in different levels.

According to an embodiment of the present application, the heterogeneous detector module includes several cuboids first crystal strips and second crystal strips which are closely arranged in sequence to construct a cuboids heterogeneous detector module and divide the heterogeneous detector module into two parts, one part of which is constituted by the first crystal strips, and the other part of which is constituted by the second crystal strips.

According to another embodiment of the present application, the first strips crystal and second crystal strips are in different sizes; wherein the size of the first crystal strips is 4.25 mm×4.25 mm×10 mm; and the size of the second crystal strips is 2.125 mm×2.125 mm×10 mm.

According to yet another embodiment of the present application, the first crystal strips amount to 80, and are arranged by 8 columns and 10 lines; the second crystal strips amount to 320 and are arranged by 16 columns and 20 lines.

According to an embodiment of the present application, multiple heterogeneous detector modules form an annular structure in the space.

According to an embodiment of the present application, several crystal strips are wedge-shaped; different kinds of crystal strips are closely arranged in sequence to constitute an arc-shaped heterogeneous detector module; and multiple heterogeneous detector modules constitute an annular three-dimensionally heterogeneous PET system.

According to another embodiment of the present application, the three-dimensionally heterogeneous PET system includes 16 heterogeneous detector modules, which constitute an annular three-dimensionally heterogeneous PET system with the inner diameter being about 213.66 mm and the axial length being about 68 mm that is the length perpendicular to the direction of cross section of the annular structure, and the axial length is the length perpendicular to the direction of cross section of the annular structure.

According to yet another example of the present application, the heterogeneous detector modules amount to two, the two heterogeneous detector modules are arranged parallel to each other and are aligned with each other in the vertical direction so as to form a flat three-dimensionally heterogeneous PET system.

The material of crystal strips in the present application is one or more selected from the group consisting of $LaBr_3$, LSO LYSO, LuYAP, $BaF_2$, GSO, LFS, $LuI_3$.

The three-dimensionally heterogeneous PET system in the present application also includes a prosthesis, which includes a chassis and several first targets and second targets with different sizes distributed on the two sides of the chassis respectively and oppositely.

The three-dimensionally heterogeneous PET system provided by the present application uses a unique way of construction, namely, crystal strips of different performances are used to form the heterogeneous detector modules. The present application effectively reduces the quantity of high performance crystal strips of the PET systems relative to the same size of imaging view area under the premise of meeting the requirements of spatial resolution of imaging area and the scope of imaging field of view. On the one hand, Compared with the high spatial resolution PET system, the present application can effectively reduce the manufacturing costs of the whole PET system without reducing spatial resolution of the PET system obviously. On the other hand, compared with the ordinary spatial resolution PET system, the present application improves the spatial resolution of the PET system by increasing small amount system cost and provides part imaging field of view with high spatial resolution in radial direction. Thus the present application provides a new development direction in the field of PET study. Moreover, the three-dimensionally heterogeneous PET system of present application can also flexibly adjust the placement of a living body according to the imaging characteristics of different organs of the living body in order to image the living body and meet the requirements of spatial resolution as to the corresponding regions.

BRIEF DESCRIPTION OF THE DRAWINGS

These and other features and advantages of this application will become more apparent to those skilled in the art from the detailed description of preferred embodiment. The drawings that accompany the description are described below.

Wherein.

DESCRIPTION OF THE PREFERRED EMBODIMENTS

The followings are used to further illustrate the present application with specific embodiments. It should be understood that the following embodiments is only used to explain the present application but not to limit the scope of the present application.

Figure 1:
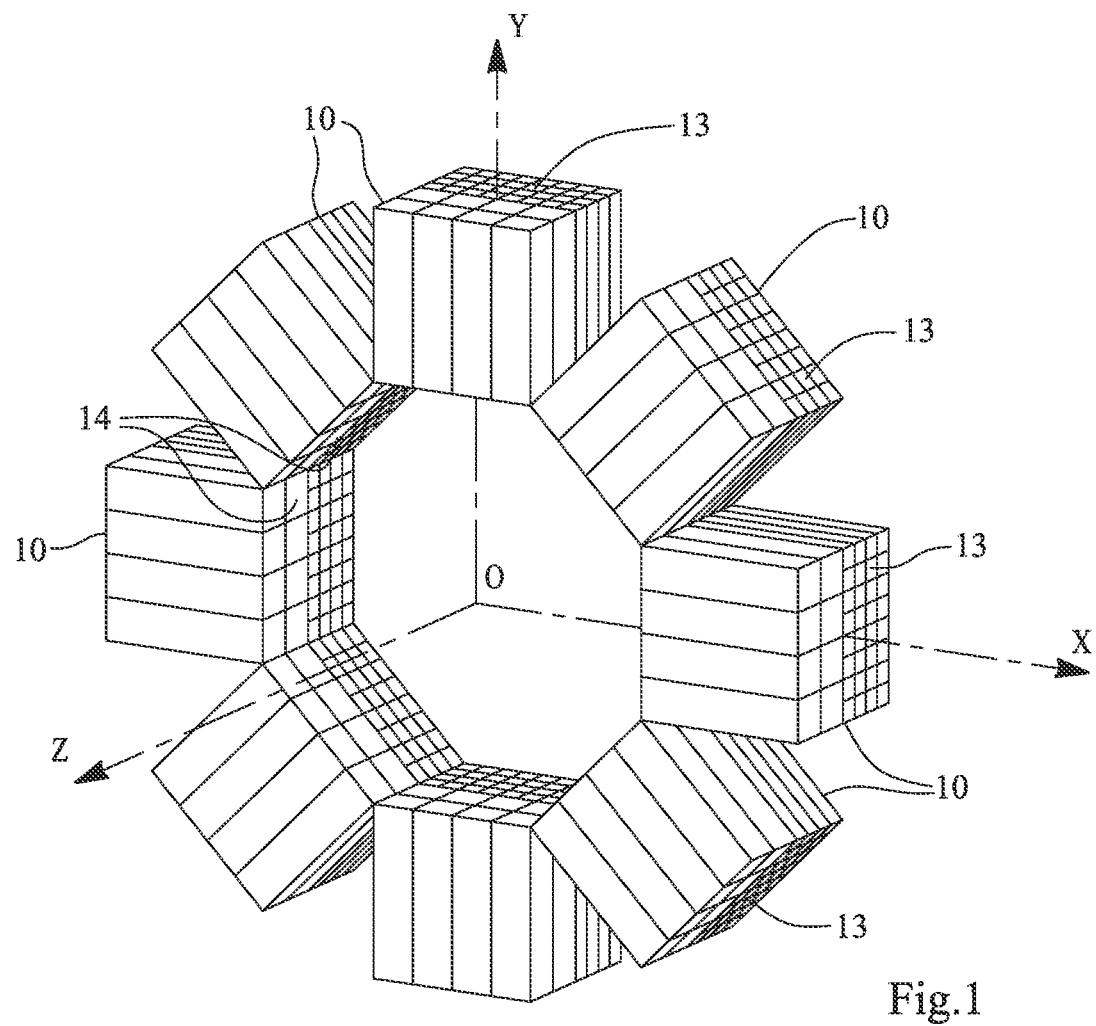
FIG. 1 is a structure schematic drawing of the detector modules of a three-dimensionally heterogeneous PET system according to an embodiment of the present application.

FIG. 1 is a layout diagram of a detector module of a three-dimensionally heterogeneous PET system according to an embodiment of the present application. As shown in FIG. 1, the three-dimensionally heterogeneous PET system 1 is provided with at least three heterogeneous detector modules 10. The heterogeneous detector modules 10 are arranged in a ring in space and each of them can either contact with each other or keep separating from each other. The skilled person in the art can determine whether the heterogeneous detector modules 10 need to be contact with each other based on actual requirements of use. Preferably, as shown in FIG. 1, the three-dimensionally heterogeneous PET system 1 of the present application includes eight heterogeneous detector modules 10, which contact with each other and form a closed annular structure in space. Specifically, when a three-dimensional coordinate system is established using the center of the ring as the point O, each heterogeneous detector module 10 includes a top surface 13 facing outwardly away from the center point O and an opposite bottom surface 14 facing inwardly toward the center point O. The bottom surfaces 14 of two adjacent heterogeneous detector modules 10 contact with each other to form an annular structure. In the embodiment shown in FIG. 1, the eight heterogeneous detector modules 10 are divided into two symmetrical annular structures by the plane XOY, one of which is a high resolution detection ring and another one is an ordinary resolution detection ring. The positions of the annular structure in the positive and negative direction of the Z-axis can be changed according to the requirements. The alternate arrangement of annular structures can also be designed, such as, high resolution detection ring-ordinary resolution detection ring-high resolution detection ring.

It should be noted that the performances of the crystal strips in the three-dimensionally heterogeneous PET system 1 are exactly the same as for any arbitrary cross section that parallels to the plane XOY. That is to say, the whole three-dimensionally heterogeneous PET system 1 can be divided into multiple rings along the different planes XOY in the Z-axis. Wherein, the performance parameters of the crystal strips are exactly the same within each of rings. However, the performance parameters of the crystal strips between each of rings can have one or more with differences.

The heterogeneous detector module 10 of the present PET system 1 includes at least two kinds of crystal strips with detection performances in different levels. The detection performance parameters include energy resolution, density, size and light output, etc. Since the detection performances of the crystal strips are divided into several levels according to the relevant indexes, the above mentioned detection performances on different levels means specifically that one or more of the performance parameters of the crystal strips are on different levels. It should be noted that the crystal strips are usually cut into cuboids, but other shapes, such as wedges, are also available in some certain situations. Actually, the skilled person in the art can choose different shapes of crystal strips as desired.

Figure 2:
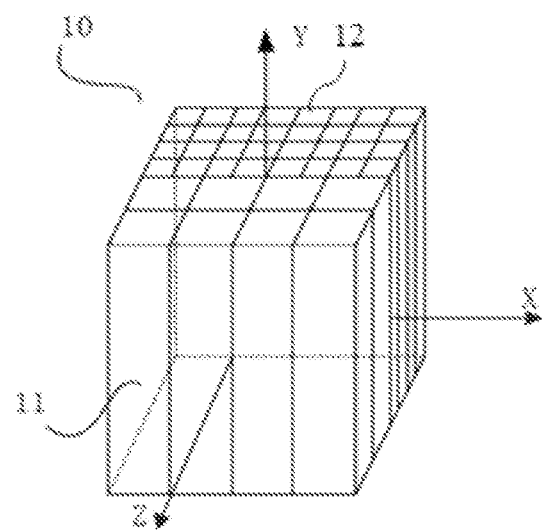
FIG. 2 is a general perspective view of the detector modules of the three-dimensionally heterogeneous PET system according to FIG. 1.

FIG. 2 is a general perspective view of the heterogeneous detector modules 10 of the three-dimensionally heterogeneous PET system 1 according to FIG. 1. In the embodiment of FIG. 2, the heterogeneous detector module 10 includes several first crystal strips 11 and second crystal strips 12 in the shape of cuboids. The detection performances of the first crystal strips 11 and the second crystal strips 12 are on different levels. Particularly, multiple first crystal strips 11 with the same detection performance are provided along the positive direction of Z-axis and multiple second crystal strips 12 with the same detection performance are provided along the negative direction of Z-axis. The first crystal strips 11 and the second crystal strips 12 are closely arranged in sequence to form a heterogeneous detector module 10 with the shape of a cuboids.

The material of the crystal strips used by the present heterogeneous detector modules 10 can be selected from the group consisting of $LaBr_3$, LSO, LYSO, LuYAP, $BaF_2$, GSO, LFS, $LuI_3$ and the like. The crystal strips of the present heterogeneous detector modules 10 are provided with different sizes which result in different performance levels. Furthermore, the crystal strips with different size can be made of crystals of either same material or different materials in order to make the crystal strips have different performance levels because different performance levels of the crystal strips can be obtained by changing the parameters of the crystal strips.

Figure 3:
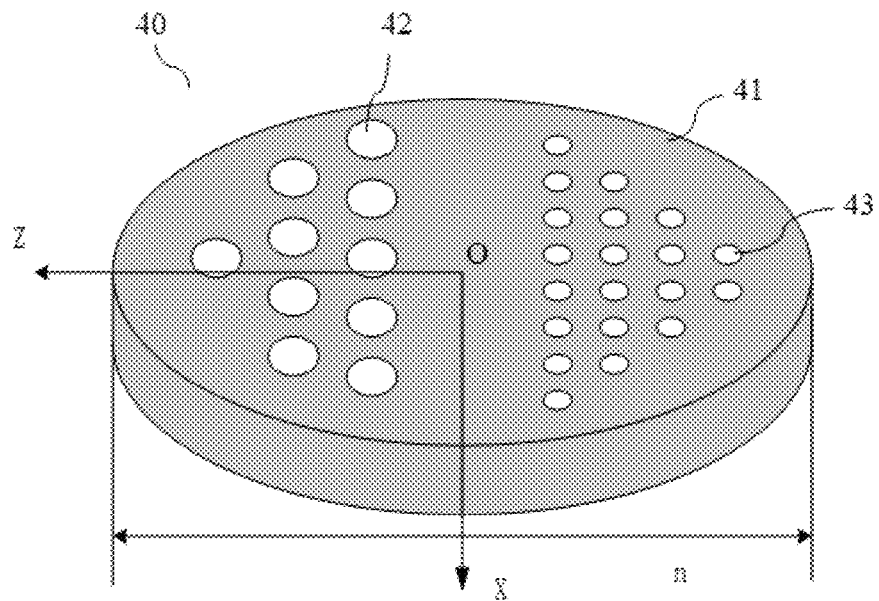
FIG. 3 is a schematic view of the prosthesis of the three-dimensionally heterogeneous PET system according to a preferred embodiment of the present application.

FIG. 3 is a general view of a prosthesis 40 of the three-dimensionally heterogeneous PET system according to a preferred embodiment of the present application. The prosthesis 40 includes a chassis 41 on which several first targets 42 and second targets 43 are distributed. The first targets 42 and the second targets 43 are provided with different sizes and are respectively and oppositely distributed on the two sides of the chassis. In the embodiment of FIG. 3, the size of the first targets 42 distributed in the left half is larger than that of the second targets 43 distributed in the right half as shown in the FIG. It is certainly that the shape of the prosthesis 40 and the distribution of the targets on it can be selected with other shapes or other distribution according to the requirement of researches or applications by the skilled person in the art.

Figure 4:
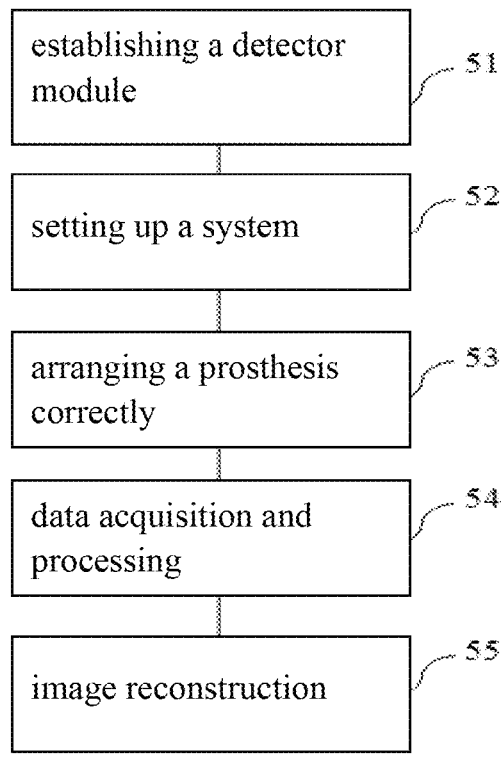
FIG. 4 is a flow diagram of use of the three-dimensionally heterogeneous PET system according to a preferred embodiment of the present application.

FIG. 4 is a use flow diagram of the three-dimensionally heterogeneous PET system 1 of the present application. As shown in FIG. 4, the method of using the three-dimensionally heterogeneous PET system 1 according to the present application includes the following steps: establishing a detector module 51, setting up a three-dimensionally heterogeneous PET system 52, arranging a prosthesis 53 correctly, data acquisition and processing 54 and image reconstruction 55.

The step of establishing a detector module 51 is illustrated by the example of the heterogeneous detector module 10 as shown in FIG. 2. When establishing a heterogeneous detector module 10, two sizes of the crystal strips are adopted, namely, the first crystal strips 11 sized with 4.25 mm×4.25 mm×10 mm and the second crystal strips 12; the sized with 2.125 mm×2.125 mm×10 mm. It should be noted that the crystal strips of this embodiment use the same material and different sizes just in order to make the spatial intrinsic resolution of the heterogeneous detector module different. However, it is not limited to the change of the size of crystal strips, any way may cause changes in aspect of the performance parameters of the crystal strips meets the need, such as changes in the size of crystal strips or changes in the material of crystal strips, etc. When establishing a heterogeneous detector module 10 as shown in FIG. 2, in particular, the part of the heterogeneous detector module 10 distributed in the positive direction of Z-axis all uses the first crystal strips 11 in the size of 4.25 mm×4.25 mm×10 mm, and the other part of which distributed in the negative direction of Z-axis all uses the second crystal strips 12 in the size of 2.125 mm×2.125 mm×10 mm. In fact, the crystal strips in a single heterogeneous detector module 10 is provided with a large number. For the convenience of illustration, the crystal strips showed by FIG. 2 do not present the actual number of the crystal strips in a single heterogeneous detector module 10. In practice, the first crystal strips 11 are distributed along the Z-axis by 10 columns which direction is the same as the Z-axis, along the X-axis by 8 lines which direction is the same as the X-axis, and the total amount of the first crystal strips 11 is 80. While the second crystal strips 12 are distributed along the Z-axis by 20 columns which direction is the same as the Z-axis, along the X-axis by 16 lines which direction is the same as the X-axis, and the total amount of the second crystal strips 12 is 320. Thus, a single heterogeneous detector module 10 includes 80 first crystal strips 11 in a relative big size and 320 second crystal strips 12 in a relative small size. It should be understood that the number of crystal strips in FIG. 2 is used to exemplify the preferred embodiment of the present application. That means the numbers of the first crystal strips and the second crystal strips of the present application can both be changed as well as the changes on numbers of the kinds of the crystal strips.

In the step of establishing the heterogeneous PET system 52, multiple heterogeneous detector modules 10 are provided to establish an annular, flat, compact, uniformly-spaced, irregular or other form heterogeneous PET system according to the characteristics of the tested body. Preferably, 16 heterogeneous detector modules 10 are used to establish a compact three-dimensionally heterogeneous PET system 1 which is sized with the inner diameter of about 213.66 mm and the axial length of 68 mm that is the length parallel to the Z-axis as shown in FIG. 2.

An arrangement of the prosthesis is required to be arranged correctly in the three-dimensionally heterogeneous PET system. In a three-dimensionally heterogeneous PET system, assuming the number of the types of crystal strips is m, at least m−1 planes parallel to the plane XOY divide the three-dimensionally heterogeneous PET system 1 into m−1 parts wherein the detection performance parameters of crystal strips are exactly the same in same part and are different in different parts. In the disc-shaped prosthesis as shown in FIG. 3, bounded by the X axis, the size of the first group of targets 42 of the prosthesis located in the part of positive direction of Z-axis is relatively big and the size of the second group of targets 43 of the prosthesis located in the part of negative direction of Z-axis is relatively small. Apparently, the region division is obvious. When arranging the prosthesis, the second group of targets 43 in a relative small size is placed in the view with a relatively high spatial resolution and the first group of targets 42 in a relative big size is placed in the view with an ordinary spatial resolution. In a word, the prosthesis is required to be arranged to guarantee the different targets of the prosthesis being located in the different imaging field of view of the three-dimensionally heterogeneous PET system. In addition, when imaging the prosthesis, the diameter n of prosthesis (as shown in FIG. 3) shall not exceed the axial length of the heterogeneous detector module that is the length parallel to the Z axis as shown in FIG. 2.

In the step of data acquisition and processing 54, an electronics system including front-end and a computer system for data processing and image reconstruction are provided for choosing time window and energy window and the calculating time meeting, energy meeting, time resolution, energy resolution and so on. The electronics system in the present application only needs to acquire the time information, energy information and location information of the event. Thus any electronics design if only meeting these requirements can be applied to the present application.

In the step of image reconstruction 55, the three-dimensionally heterogeneous PET system can conduct image reconstruction by using a variety of reconstruction methods including Maximum Likelihood Expectation Maximization algorithm (ML-EM algorithm), Ordered Subsets Expectation Maximization algorithm (OSEM algorithm) and relatively simple direct backprojection algorithm, such as FBP. The reconstruction method is not unique and ML-EM algorithm and OSEM algorithm are preferably used in the image reconstruction in the present application.

Figure 5:
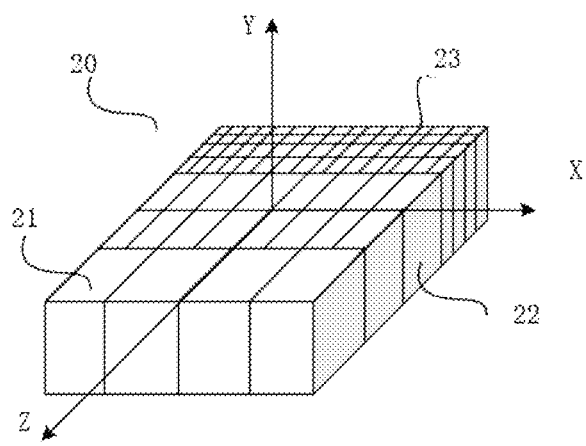
FIG. 5 is a schematic perspective view of the detector module of the three-dimensionally heterogeneous PET system according to another embodiment of the present application.

The present application uses heterogeneous detector module to construct a three-dimensionally heterogeneous PET system. It should be understood that the shape of the PET system is not only limited to be annular but also flat, compact, uniformly-spaced, irregular or other shape by using heterogeneous detector module according to the characteristics of the tested body. FIG. 5 is a general perspective view of the heterogeneous detector module 20 of the three-dimensionally heterogeneous PET system according to another embodiment of the present application. In the embodiment as shown in FIG. 5, the heterogeneous detector module 20 of the present three-dimensionally heterogeneous PET system includes several first crystal strips 21, several second crystal strips 22 and several third crystal strips 23 which are all cuboid-shaped with different sizes and different detection performance levels. In specifically, the first crystal strips 21, the second crystal strips 22 and the third crystal strips 23 are closely arranged in sequence and constitute a flat heterogeneous detector module 20. The two such heterogeneous detector modules 20 on top and the bottom respectively are arranged parallel to each other and aligned to each other in the vertical direction, thus a flat heterogeneous PET system is formed.

Figure 6:
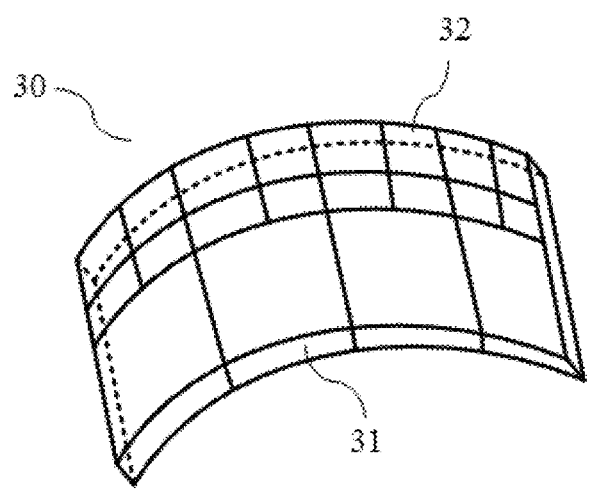
FIG. 6 is a schematic perspective view of the detector module of the three-dimensionally heterogeneous PET system according to yet another embodiment of the present application.

FIG. 6 is a general perspective view of the heterogeneous detector module 30 of the three-dimensionally heterogeneous PET system according to yet another embodiment of the present application. In this embodiment, the heterogeneous detector module 30 includes several first crystal strips 31 and several second crystal strips 32 both in wedge shape and with different sizes have different detection performance levels. In specifically, the first crystal strips 31 and the second crystal strips 32 are closely arranged in sequence and constitute an arc-shape heterogeneous detector module 30. Multiple such heterogeneous detector modules 30 can constitute an annular heterogeneous PET system.

The three-dimensionally heterogeneous PET system provided by the present application uses a unique way of construction, namely, uses a variety of crystal strips with different performances to construct the heterogeneous detector module. Under the condition of the same structure, the present application can effectively reduce the manufacturing cost of the whole PET system without obviously reducing the spatial resolution of the PET system compared with the high spatial resolution PET system, and can improve the spatial resolution of the PET system only by increasing relative small cost and provide part imaging field of views with high spatial resolution in radial direction compared with the ordinary spatial resolution PET system. In addition, the present application can take advantage of combining a high performance detector module with a conventional PET system based on the normal PET system, so as to restructure a new heterogeneous PET system conveniently.

Moreover, the three-dimensionally heterogeneous PET system can also flexibly adjust the placement of the living according to the imaging characteristics of different organs of the living in order to image the living and meet the requirements of the corresponding regions in aspect of spatial resolution.

The foregoing application has been described in accordance with the relevant legal standard, thus the description is exemplary rather than limiting in nature. Variations and modifications to the disclosed embodiment may become apparent to those skilled in the art and do come within the scope of the application. Accordingly, the scope of legal protection afforded this application can only be determined by studying the following claims.

What is claimed is:

1. A three-dimensionally heterogeneous PET system, comprising:
   at least two heterogeneous detector modules, each of which being disposed about a common axis and including a plurality of crystal strips;
   wherein the plurality of crystal strips are closely arranged and include at least two different kinds of crystal strips, each being made of a same material and having a different size to provide a different detection performance level, wherein the plurality of crystal strips includes at least two crystal strips having a same kind and providing a same detection performance level, wherein the detection performance levels relate to one or more of: energy resolution, density, size, and light output;

wherein crystal strips of the plurality of crystal strips located in a same plane extending perpendicular to the common axis are each crystal strips of a same kind, and crystal strips of the plurality of crystal strips located in different planes extending perpendicular to the common axis include the at least two different kinds of crystal strips.

2. The three-dimensionally heterogeneous PET system according to claim 1, wherein the plurality of crystal strips includes a plurality of first crystal strips and a plurality of second crystal strips, wherein each crystal strip of the plurality of first crystal strips has a cuboid shape, and the plurality of first crystal strips are closely arranged in sequence to form a first block, wherein each crystal strip of the plurality of second crystal strips has a cuboid shape, and the plurality of second crystal strips are closely arranged in sequence to form a second block, and wherein at least one heterogeneous detector module of the at least two heterogeneous detector modules includes the first block disposed adjacent to the second block.

3. The three-dimensionally heterogeneous PET system according to claim 2, wherein each of the first crystal strips is 4.25 mm×4.25 mm×10 mm and each of the second crystal strips is 2.125 mm×2.125 mm×10 mm.

4. The three-dimensionally heterogeneous PET system according to claim 2, wherein the first block includes 80 of the first crystal strips arranged in 8 columns and 10 lines, and wherein the second block includes 320 of the second crystal strips arranged in 16 columns and 20 lines.

5. The three-dimensionally heterogeneous PET system according to claim 1, wherein the at least two heterogeneous detector modules form an annular structure.

6. The three-dimensionally heterogeneous PET system according to claim 5, wherein each crystal strip of the plurality of crystal strips has a wedge-shape and the plurality of crystal strips includes the at least two different kinds of the crystal strips closely arranged in sequence to constitute an arc-shaped heterogeneous detector module of the at least two heterogeneous detector modules, and wherein multiple heterogeneous detector modules of the at least two heterogeneous detector modules are combined to form an annular structure of the three-dimensionally heterogeneous PET system.

7. The according to claim 5, wherein the annular structure of the three-dimensionally heterogeneous PET system includes 16 of the heterogeneous detector modules, and wherein the annular structure of the three-dimensionally heterogeneous PET system has an inner diameter of about 213.66 mm and an axial length of about 68 mm.

8. The three-dimensionally heterogeneous PET system according to claim 1, wherein the at least two heterogeneous detector modules are arranged parallel and aligned to each other in a vertical direction so as to form the three-dimensionally heterogeneous PET system with a flat configuration.

9. The three-dimensionally heterogeneous PET system according to claim 1, wherein the plurality of crystal strips is made of one or more materials selected from the group consisting of: LaBr3, LSO, LYSO, Lu YAP, BaF2, GSO, LFS and LuI3.

10. The three-dimensionally heterogeneous PET system according to claim 1, further comprising a prosthesis including a chassis defining two regions, with several first targets and several second targets, each of the first targets having a first size and being located on one of the two regions, and each of the second targets having a second size, different from the first size, and being located on an opposite one of the two regions from the first targets.

* * * * *